US005837480A

United States Patent [19]
Sacchettini et al.

[11] Patent Number: 5,837,480
[45] Date of Patent: Nov. 17, 1998

[54] METHOD AND COMPOUNDS FOR INHIBITING LIPID BIOSYNTHESIS OF BACTERIA AND PLANTS

[75] Inventors: James Sacchettini, New Rochelle; John Blanchard, Pelham Manor; William R. Jacobs, Jr., City Island, all of N.Y.

[73] Assignee: Albert Einstein College of Medicine of Yeshiva University, a Division of Yeshiva University, Bronx, N.Y.

[21] Appl. No.: 700,306

[22] Filed: Aug. 21, 1996

Related U.S. Application Data

[62] Division of Ser. No. 234,011, Apr. 28, 1994.
[51] Int. Cl.$^6$ .............................. C12Q 1/26; C12Q 1/04; C12Q 1/00; G01N 33/53
[52] U.S. Cl. .............................. 435/25; 435/34; 435/189; 435/968; 435/863; 435/864; 435/865; 435/866; 435/4; 435/32; 435/7.1; 435/7.4; 514/354; 536/23.7; 536/24.33; 504/716; 504/117
[58] Field of Search .............................. 435/25, 34, 189, 435/968, 863, 864, 865, 866, 4, 32, 7.1, 7.4; 514/354; 536/23.7, 24.32, 24.33; 504/116, 117

[56] References Cited

U.S. PATENT DOCUMENTS

| | | | |
|---|---|---|---|
| 4,886,646 | 12/1989 | Carter et al. | 117/202 |
| 4,919,899 | 4/1990 | Herrmann et al. | 422/245.1 |
| 4,990,216 | 2/1991 | Fujita et al. | 117/68 |
| 5,556,778 | 9/1996 | Sacchettini | 435/189 |

OTHER PUBLICATIONS

Lefford et al., *Tubercle*, vol. 47, p. 109 (1966). Month not available.
Stoecle et al., *J. Inf. Dis.*, vol. 168, p. 1063 (1993). Month not available.
Middlebrook, *Am. Rev. Tuberc.*, vol. 65, pp. 765–767. Month not available.
Zhang et al., *Molec. Microbiol.*, vol. 8, pp. 521–529 (1993). Month not available.
Canetti, *Am. Rev. Respir. Dis.*, vol. 92, p. 687 (1965). Month not available.
Grumbach, *Rev. Tuber.*, vol. 25, p. 1365 (1961). Month not available.
Lefford, *Tubercle*, vol. 47, p. 198 (1966). Month not available.
Hok, *Am. Rev. Respir. Rev.*, vol. 90, pp. 468–469 (1964). Month not available.
Banerjee et al., *Science*, vol. 263, pp. 227, 230 (Jan. 1994).
Banerjee et al. (1994) *Science*, 263, "inhA, a Gene Encoding a Target for Isoniazid and Ethionamide in *Mycobacterium Tuberculosis*", pp. 227–230. Month not available.
Dessen et al. (1995) *Science*, 267, "Crystal Structure and Function of the Isoniazid Target of *Mycobacterium tuberculosis*", pp. 1638–1641. Month not available.
McPherson (1976) *Meth. Biochem. Anal.*, 23, "The Growth and Preliminary Investigation of Protein and Nucleic Acid Crystals for X–Ray Diffraction Analysis", pp. 249–345. Month not available.
Delucas et al. (1987) *Trends Biochem. Technol.*, 5, "New Directions in Prottein Crystal Growth", pp. 188–193. Month not available.
Giegé et al. (1989) *Trends Biochem. Technol.*, 7, "Crystallogenesis of Proteins", pp. 277–282. Month not available.

*Primary Examiner*—Louise Leary
*Attorney, Agent, or Firm*—Amster, Rothstein & Ebenstein

[57] ABSTRACT

This invention relates to InhA enzyme crystals and to methods of growing said crystals. This invention is further directed to the utilization of said crystals to determine the three dimensional structure of InhA enzyme utilizing heavy atom derivatives of said crystals, and to the identification and development of compounds which inhibit the biochemical activity of InhA enzyme in bacteria and plants.

8 Claims, 12 Drawing Sheets

ENOYL REDUCTASE MECHANISM

METHOD AND COMPOUNDS FOR INHIBITING LIPID BIOSYNTHESIS OF BACTERIA AND PLANTS

This is a divisional of copending application Ser. No. 8/234,011 pending filed on Apr. 28, 1994.

STATEMENT OF GOVERNMENT INTEREST

This invention was made with government support under NIH Grant Numbers AI33696 and AI27160. As such, the government has certain rights in the invention.

FIELD OF THE INVENTION

This invention is directed to InhA crystals which are suitable for x-ray diffraction studies and to a method of producing said InhA crystals and heavy-atom derivatives thereof. The crystals may be used to determine the three dimensional structure of InhA enzyme. Once the three dimensional structure of InhA enzyme is known, compounds which inhibit the biochemical activity of InhA enzyme in bacteria may be developed and administered to treat bacterial infection. In addition, this invention is directed to methods of determining whether compounds are useful as bacteriocidal or herbicidal agents utilizing InhA.

BACKGROUND OF THE INVENTION

Tuberculosis remains the largest cause of death in the world from a single infectious disease and is responsible for one in four avoidable adult deaths in developing countries. Infection with drug-sensitive strains of *Mycobacterium tuberculosis* can be effectively cured with a combination of isoniazid, ethionamide, rifampicin and pyrazinamide. However, the emergence of multiple drug resistant strains of *M. tuberculosis* has resulted in fatal outbreaks in the United States.

Isoniazid was first reported to be active against *M. tuberculosis* in 1952, when it was shown to have a highly specific activity against *M. tuberculosis* and *M. bovis*, with less but considerable activity against other mycobacteria. Although isoniazid is one of the most widely used anti-tuberculosis drugs for both therapy and prophylaxis, its precise target of action on *Mycobacterium tuberculosis* has remained unknown. Isoniazid was first synthesized as an organic compound in 1912, but it was not until 1952 that three independent groups discovered that it had anti-tuberculosis activity. The discovery that ethionamide had anti-tuberculosis activity was predicated on the discovery that nicotinamide showed some tuberculostatic activity against *M. tuberculosis*.

Resistance to isoniazid was first reported in 1953, but in recent years has been as high as 26% in some areas of the United States. A fraction of isoniazid-resistant strains had been shown to be associated with a loss of catalase activity (see Lefford et al., *Tubercle*, Vol. 47, p. 109 (1966) and Stoecle et al., *J. Inf. Dis.*, Vol. 168, p. 1063 (1993)). The catalase gene (katG) was recently cloned and deletions of this gene were shown to be correlated with isoniazid resistance in certain *M. tuberculosis* isolates (see Zhang et al., *Nature*, Vol. 358, pp. 591–593 (1992)). Furthermore, transfer of the *M. tuberculosis* katG gene to isoniazid-resistant *M. smegmatis* strains results in the acquisition of isoniazid-sensitivity, suggesting that the presence of the catalase activity results in the sensitivity of *M. tuberculosis* to isoniazid (see Middlebrook, *Am. Rev. Tuberc.*, Vol. 65, pp. 765–767 and Zhang et al., *Molec. Microbiol.*, Vol. 8, pp. 521–529 (1993)).

Although catalase may be important to the action of isoniazid, it does not appear to be the target of action of isoniazid. Isoniazid-resistance can be accounted for by the loss of catalase activity, however only 25% of isoniazid-resistant isolates appear to be catalase negative. Previous studies have shown that low-level isoniazid-resistance correlated not with the loss of catalase activity, but rather with the co-acquisition of ethionamide resistance (see Canetti, *Am. Rev. Respir. Dis.*, Vol. 92, p. 687 (1965); Grumbach, *Rev. Tuber.*, Vol. 25, p. 1365 (1961); Lefford, *Tubercle*, Vol. 47, p. 198 (1966) and Hok, *Am. Rev. Respir. Rev.*, Vol. 90, pp. 468–469 (1964)).

Drug resistance can often be mediated by the accumulation of mutations in the gene encoding the targets that result in reduced binding of drugs for their targets. For example, rifampicin resistance is often mediated by mutations in the gene encoding the β' subunit of RNA polymerase. Alternatively, trimethoprim resistance can be mediated by mutations causing amplification in a target dihydrofolate reductase.

Without the availability of genetic systems for the mycobacteria, the identification of the precise target of action of isoniazid and ethionamide could not be determined. Hence, it has been desirable to identify the specific point mutations that confer resistance to isoniazid and ethionamide in *M. tuberculosis*. The enzyme which is the target of action of isoniazid has been identified and denoted InhA, and the gene which encodes the enzyme InhA has been denoted inhA (see Banerjee et al., *Science*, Vol. 263, pp. 227,230 (January 1994)). As used herein, "InhA" includes InhA enzyme and any mutants thereof.

The inhA gene shares significant homology with a gene that codes for the EnvM protein from *E. coli* and *Salmonella typhimurium*, which protein is known to be involved in fatty acid (lipid) biosynthesis. Mycolic acids are long chain fatty acids. The enzyme InhA encoded by the inhA gene is necessary for mycolic acid biosynthesis.

Mycolic acids, also referred to herein as lipids, are long chain fatty acids (60 to 80 carbons in lengths) that are major constituents of a mycobacterial cell wall. They are thought to be the chemical moeities responsible for the characteristic acid-fastness of mycobacteria and provide the waxy layer of mycobacterial cells. Mycolic acids have been demonstrated to have covalent linkages to arabino-galactans and thus maintain the integrity of the mycobacterial cell wall. Inhibition in their syntheses would result in a disruption of the cell wall and the death of the mycobacteria. Since mycolic acids are unique to the mycobacteria, mycolic acid biosynthetic enzymes are excellent targets for development of drugs useful in the treatment of mycobacterial infection. However, in order to develop drugs capable of inhibiting InhA activity, it is necessary to know the resident enzymatic activity of the gene product and/or to have InhA crystals from which the three dimensional structure of InhA enzyme can be determined.

It is therefore an object of this invention to provide InhA enzyme crystals.

It is another object of this invention to provide a method of producing InhA enzyme crystals.

It is a further object of this invention to provide a method of producing heavy metal derivatives of InhA enzyme crystals.

It is a still further object of this invention to provide a method of determining whether a compound is useful as a bacteriocide or a herbicide.

SUMMARY OF THE INVENTION

This invention is directed to InhA enzyme crystals and methods of producing said crystals. This invention is further directed to the use of said crystals to determine the three dimensional structure of InhA enzyme, and to the use of said three dimensional structure to develop compounds which inhibit the biochemical activity of InhA enzyme in bacteria and plants. In addition, this invention is directed to methods of determining whether a compound is useful as a bacteriocide or a herbicide.

This invention provides for several InhA crystals. Some of the InhA crystals of this invention are plate-shaped, have the space group C2, have a size of about 0.3×0.5×0.5 mm, are suitable for x-ray diffraction to at least 2.0 Å and have the following unit cell constants: a=101.1 Å; b=83.4 Å; c=192.9 Å; $\beta=95°$; and $\alpha=\gamma=90°$. Other InhA crystals provided herein are hexagonal-shaped, have the space group P6$_2$22, have a size of about 0.5×0.5×0.2 mm, are suitable for x-ray diffraction, and have the following unit cell constants: a=b=100.14 Å; c=140.4 Å; $\alpha=\beta=90°$; and $\gamma=120°$. Still other crystals provided herein are parallelepiped-shaped, have the space group P2$_1$, have a size of about 0.3×0.3×0.6 mm, are suitable for x-ray diffraction to at least 2.0 Å and have the following unit cell constants: a=69 Å; b=116 Å; c=65 Å; $\beta=97.8°$; and $\alpha=\gamma=90°$.

This invention is further directed to a method of growing InhA crystals. A solution containing InhA and NADH is provided, and a precipitant solution containing methyl pentane diol, a salt and a buffer is also provided. A droplet of the InhA solution is mixed with a droplet of the precipitant solution to obtain a mixed droplet solution. The mixed droplet solution is suspended over a well of precipitant solution in a sealed container, wherein the vapor pressure of the precipitant solution is lower than the vapor pressure of the mixed droplet solution. The mixed droplet solution is allowed to stand for a period of time sufficient for InhA enzyme crystals to grow.

InhA enzyme crystals can then be studied to determine the three dimensional structure of InhA enzyme. Once the enzymatic activity and the three dimensional structure of InhA enzyme are known, compounds can be developed which inhibit the activity of InhA enzyme in bacteria and plants.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein.

DETAILED DESCRIPTION OF THE INVENTION

Figure 1:
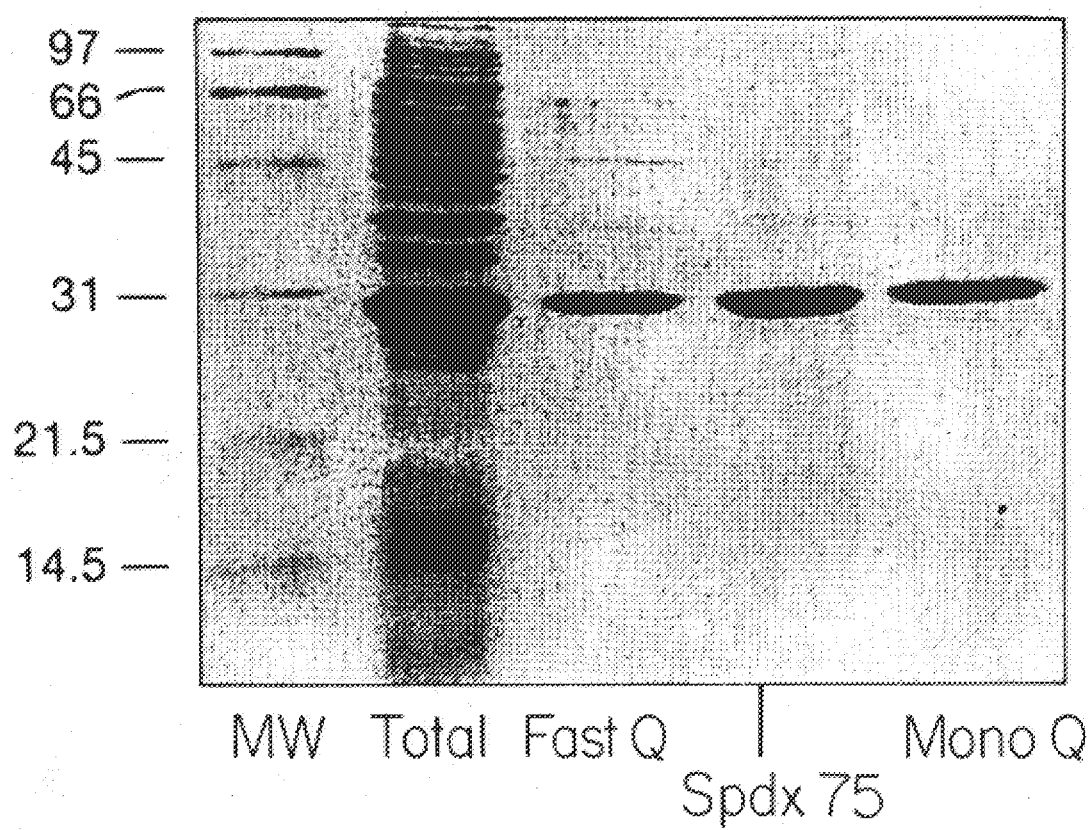
FIG. 1 represents SDS-PAGE of InhA, which shows no protein impurities.

As previously discussed, the sequence of InhA has been determined. The inventors have overexpressed and purified InhA utilizing the nucleic acid sequence of InhA. The sequence of InhA is as follows:

SEQ ID NO: 1

| | | | | | | |
|---|---|---|---|---|---|---|
| AGCGCGACAT | ACCTGCTGCG | CAATTCGTAG | GGCGTCAATA | CACCCGCAGC | CAGGGCCTCG | 60 |
| CTGCCCAGAA | AGGGATCCGT | CATGGTCGAA | GTGTGCTGAG | TCACACCGAC | AAACGTCACG | 120 |
| AGCGTAACCC | CAGTGCGAAA | GTTCCCGCCG | GAAATCGCAG | CCACGTTACG | CTCGTGGACA | 180 |
| TACCGATTTC | GGCCCGGCCG | CGGCGAGACG | ATAGGTTGTC | GGGGTGACTG | CCACAGCCAC | 240 |
| TGAAGGGGCC | AAACCCCCAT | TCGTATCCCG | TTCAGTCCTG | GTTACCGGAG | GAAACCGGGG | 300 |
| GATCGGGCTG | GCGATCGCAC | AGCGGCTGGC | TGCCGACGGC | CACAAGGTGG | CCGTCACCCA | 360 |
| CCGTGGATCC | GGAGCGCCAA | AGGGGCTGTT | TGGCGTCGAA | TGTGACGTCA | CCGACAGCGA | 420 |
| CGCCGTCGAT | CGCGCCTTCA | CGGCGGTAGA | AGAGCACCAG | GGTCCGGTCG | AGGTGCTGGT | 480 |

-continued
SEQ ID NO: 1

| | | | | | | |
|---|---|---|---|---|---|---|
| GTCCAACGCC | GGCCTATCCG | CGGACGCATT | CCTCATGCGG | ATGACCGAGG | AAAAGTTCGA | 540 |
| GAAGGTCATC | AACGCCAACC | TCACCGGGGC | GTTCCGGGTG | GCTCAACGGG | CATCGCGCAG | 600 |
| CATGCAGCGC | AACAAATTCG | GTCGAATGAT | ATTCATAGGT | TCGGTCTCCG | GCAGCTGGGG | 660 |
| CATCGGCAAC | CAGGCCAACT | ACGCAGCCTC | CAAGGCCGGA | GTGATTGGCA | TGGCCCGCTC | 720 |
| GATCGCCCGC | GAGCTGTCGA | AGGCAAACGT | GACCGCGAAT | GTGGTGGCCC | CGGGCTACAT | 780 |
| CGACACCGAT | ATGACCCGCG | CGCTGGATGA | GCGGATTCAG | CAGGGGGCGC | TGCAATTTAT | 840 |
| CCCAGCGAAG | CGGGTCGGCA | CCCCCGCCGA | GGTCGCCGGG | GTGGTCAGCT | TCCTGGCTTC | 900 |
| CGAGGATGCG | AGCTATATCT | CCGGTGCGGT | CATCCCGGTC | GACGGCGGCA | TGGGTATGGG | 960 |
| CCACTGACAC | AACACAAGGA | CGCACATGAC | AGGACTGCTG | GACGGCAAAC | GGATTCTGGT | 1020 |
| TAGCGGAATC | ATCACCGACT | CGTCGATCGC | GTTTCACATC | GCACGGGTAG | CCCAGGAGCA | 1080 |
| GGGCGCCCAG | CTGGTGCTCA | CCGGGTTCGA | CCGGCTGCGG | CTGATTCAGC | GCATCACCGA | 1140 |
| CCGGCTGCCG | GCAAAGGCCC | CGCTGCTCGA | ACTCGACGTG | CAAAACGAGG | AGCACCTGGC | 1200 |
| CAGCTTGGCC | GGCCGGGTGA | CCGAGGCGAT | CGGGGCGGGC | AACAAGCTCG | ACGGGGTGGT | 1260 |
| GCATTCGATT | GGGTTCATGC | CGCAGACCGG | GATGGGCATC | AACCCGTTCT | TCGACGCGCC | 1320 |
| CTACGCGGAT | GTGTCCAAGG | GCATCCACAT | CTCGGCGTAT | TCGTATGCTT | CGATGGCCAA | 1380 |
| GGCGCTGCTG | CCGATCATGA | ACCCCGGAGG | TTCCATCGTC | GGCATGGACT | TCGACCCGAG | 1440 |
| CCGGGCGATG | CCGGCCTACA | ACTGGATGAC | GGTCGCCAAG | AGCGCGTTGG | AGTCGGTCAA | 1500 |
| CAGGTTCGTG | GCGCGCGAGG | CCGGCAAGTA | CGGTGTGCGT | TCGAATCTCG | TTGGCGCAGG | 1560 |
| CCCTATCCGG | ACGCTGGCGA | TGAGTGCGAT | CGTCGGCGGT | GCGCTCGGCG | AAGAGGCCGG | 1620 |
| CGCCCAGATC | CAGCTGCTCG | AGGAGGGCTG | GGATCAGCGC | GCTCCGATCG | GCTGGAACAT | 1680 |
| GAAGGATGCG | ACGCCGGTCG | CCAAGACGGT | GTGCGCGCTG | CTGTCTGACT | GGCTGCCGGC | 1740 |
| GACCACGGGT | GACATCATCT | ACGCCGACGG | CGGCGCGCAC | ACCCAATTGC | TCTAGAACGC | 1800 |
| ATGCAATTTG | ATGCCGTCCT | GCTGCTGTCG | TTCGGCGGAC | CGGAAGGGCC | CGAGCAGGTG | 1860 |
| CGCCCGTTCC | TGGAGAACGT | TACCCGGGGC | CGCGGTGTGC | CTGCCGAACG | GTTGGACGCG | 1920 |
| GTGGCCGAGC | ACTACCTGCA | TTTCGGTGGG | GTATCACCGA | TCAATGGCAT | TAATCGCACA | 1980 |
| CTGATCGCGG | AGCTGGAGGC | GCAGCAAGAA | CTGCCGGTGT | ACTTCGGTAA | CCGCAACTGG | 2040 |
| GAGCCGTATG | TAGAAGATGC | CGTTACGGCC | ATGCGCGACA | ACGGTGTCCG | GCGTGCAGCG | 2100 |

-continued
SEQ ID NO: 1

| | | | | | | |
|---|---|---|---|---|---|---|
| GTCTTTGCGA | CATCTGCGTG | GAGCGGTTAC | TCGAGCTGCA | CACAGTACGT | GGAGGACATC | 2160 |
| GCGCGGCCCC | CCGCGCGGCC | GGGCGCGACG | CGCCTGAACT | GGTAAAACTG | CGGCCCTACT | 2220 |
| TCGACCATCC | GCTGTTCGTC | GAGATGTTCG | CCGACGCCAT | CACCGCGGCC | GCCGCAACCG | 2280 |
| TGCGCGGTGA | TGCCCGGCTG | GTGTTCACCG | CGCATTCGAT | CCCGACGGCC | GCCGACCGCC | 2340 |
| GCTGTGGCCC | CAACCTCTAC | AGCCGCCAAG | TCGCCTACGC | CACAAGGCTG | GTCGCGGCCG | 2400 |
| CTGCCGGATA | CTGCGACTTT | GACCTGGCCT | GGCAGTCGAG | ATCGGGCCCG | CCGCAGGTGC | 2460 |
| CCTGGCTGGA | GCCAGACGTT | ACCGACCAGC | TCACCGGTCT | GGCTGGGGCC | GGCATCAACG | 2520 |
| CGGTGATCGT | GTGTCCCATT | GGATTCGTCG | CCGACCATAT | CGAGGTGGTG | TGGGATCTCG | 2580 |
| ACCACGAGTT | GCGATTACAA | GCCGAGGCAG | CGGGCATCGC | GTACGCCCGG | GCCAGCACCC | 2640 |
| CCAATGCCGA | CCCGCGGTTC | GCTCGACTAG | CCAGAGGTTT | GATCGACGAA | CTCCGTTACG | 2700 |
| GCCGTATACC | TGCGCGGGTG | AGTGGCCCCG | ATCCGGTGCC | GGGCTGTCTG | TCCAGCATCA | 2760 |
| ACGGCCAGCC | ATGCCGTCCG | CCGCACTGCG | TGGCTAGCGT | CAGTCCGGCC | AGGCCGAGTG | 2820 |
| CAGGATCGCC | GTGACCGCGG | ACATCCGGGC | CGAGCGCACC | ACGGCGGTCA | ACGGTCTCAA | 2880 |
| CGCATCGGTG | GCACGCTGAG | CGTCCGACAA | CGACTGCGTT | CCGATCGGCA | ATCGACTCAG | 2940 |
| CCCGGCACTG | ACCGCGATGA | TCGCATCGAC | GTGCGCGGCA | TTCTCGAGCA | CCCGCAATGC | 3000 |
| GCGCGATGGC | GCGTGGTCGG | GAACCCGGTG | TTGCCGTGAC | GATTCGAGCA | ACTGCTCGAC | 3060 |
| GAGGCCACGG | GGCTTGGCGA | CGTCGCTAGA | TCCCAGTCCG | ATGGTGCTCA | AGGCTTCGGC | 3120 |

Two mechanisms of isoniazid and ethionamide resistance mediated through the inhA gene have been determined. One mechanism involves the generation of a mutation that causes an amino acid substitution in the InhA protein. The other mechanism of resistance is mediated by overexpression of the InhA protein. This mechanism, which is analogous to amplification of the dihydrofolate reductase gene, results in the titration of the isoniazid or ethionamide by numerous copies of the InhA protein. Both of these mechanisms demonstrate that InhA is the target of action for both ethionamide and isoniazid.

The protein encoded by mabA additionally exhibits significant homology to genes involved in fatty acid biosynthesis (the highest identity score is 46% over 124 amino acids with the, fabG gene of E. coli, acetoacetyl CoA reductase). The similarities of the InhA and the MabA ORFs to genes of fatty acid biosynthesis are consistent with the hypothesis that isoniazid inhibits an enzyme involving mycolic acid (long chain fatty acids of mycobacterial cell-wall) biosynthesis. Cell free extracts either from resistant mutant $mc^2 651$ or from resistant merodiploids containing multi-copy plasmids with the inhA gene showed marked resistance to isoniazid-inhibition of mycolic acid biosynthesis compared to the wild-type $mc^2 155$ control. The observation that the likely only genetic difference between $mc^2$ 155 and $mc^2$ 651 is in the inhA gene indicates that InhA is involved in mycolic acid biosynthesis. The inhA gene was expressed, purified and characterized by the inventors, as described below.

EXAMPLE 1

Determination of Enzymatic Activity of InhA

InhA of the M. tuberculosis H37 Rv strain was amplified by PCR, and cloned initially into the pBluescript KSII vector, and subsequently reamplified using primers which contained NcoI and Bam Hl restriction fragment sites. The PCR product was ligated into a pET-15d vector, which was previously treated with NcoI and Bam Hl, and transformed first into *E. coli* strain DH5α, and subsequently into BL21 (DE3). No mutations were introduced into the inhA gene as a result of these manipulations, as evidenced by sequencing of the gene. Growth of these cells and induction with 1 mM IPTG resulted in the expression of the inhA gene as a soluble protein of 28,500 daltons, comprising 20–30% of the total soluble protein as determined by SDS-PAGE. In order to prepare sufficient protein for purification and enzymatic characterization, four liters of media were innoculated, grown to an OD of 1–1.5 and induced with IPTG. After four hours, approximately 40 grams of cells were collected by centrifugation, and frozen at −70° C. All subsequent purification steps were performed at 4° C.

Classic protein purification methods were used throughout, and all fractions were analyzed by SDS-PAGE. Cells were broken by passage through a French press at 18,000 psi, and the cell-free clear supernatant obtained after centrifugation was treated with streptomycin sulfate (1% final) to remove nucleic acids. The supernatant obtained after centrifugation was dialyzed, and applied to a Fast Q anion exchange column. Proteins were eluted using a NaCl gradient, and fractions containing the 28.5 kD protein band were pooled, dialyzed, concentrated by ultrafiltration, and applied to a Superdex 75 gel filtration column. The InhA protein eluted from this gel filtration column at an apparent native molecular weight of 64,000 kDa, suggesting that it functions as a dimer. Once again, fractions containing the 28.5 kD protein band were pooled, and applied to a 1×10 Mono Q high performance anion exchange column. Elution with a nonlinear NaCl gradient yielded fractions which exhibited a single band on SDS-PAGE with Coomassie Blue staining, and with no demonstrable protein impurities (see FIG. 1). Amino terminal sequencing confirmed the identity of this homogeneous protein as the inhA gene product. The purified protein exhibits a molecular mass of 28,547 daltons as determined by electrospray mass spectrometry, in agreement with the mass predicted from the gene sequence. The first 19 amino acids were sequenced using automated Edman degradation and found to be identical to those predicted from the gene sequence. Approximately 70 mg of homogeneous InhA were obtained from 30 grams of cells.

Figure 2:
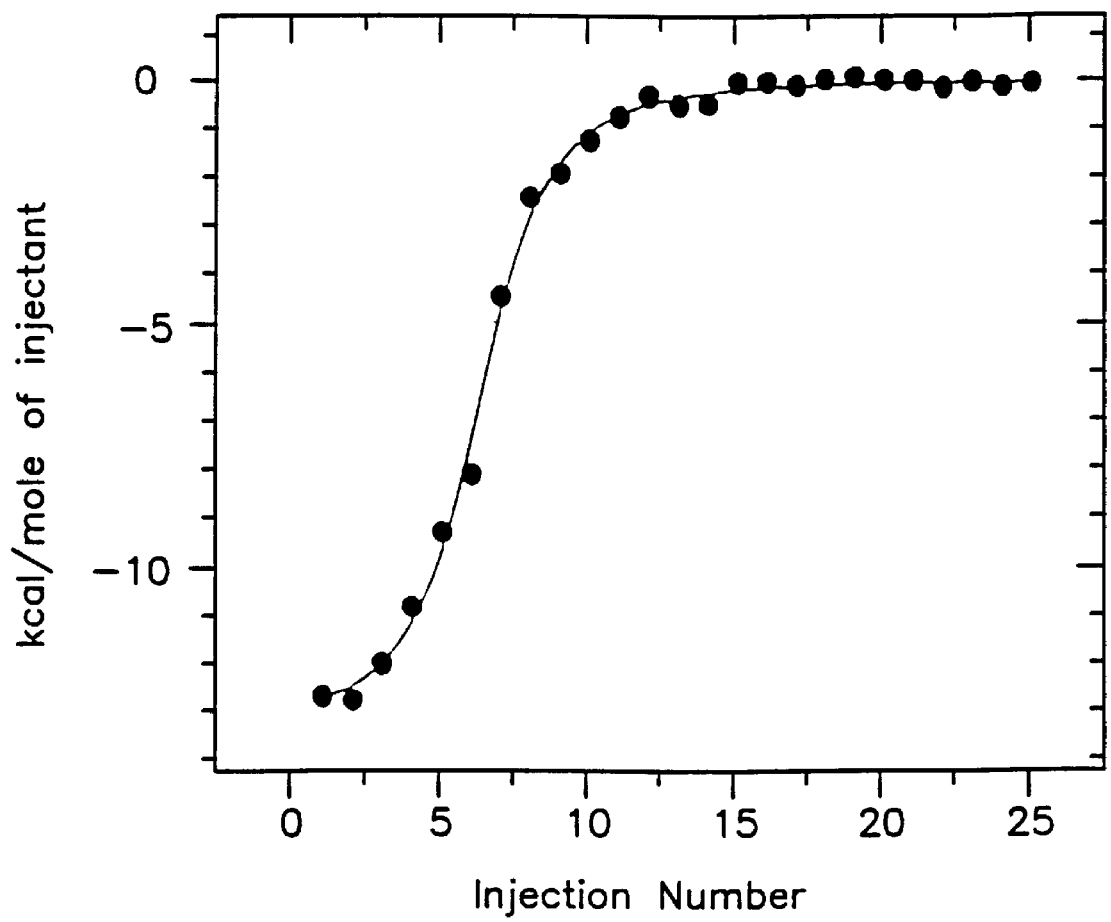
FIG. 2 represents a titration calorimetric isotherm for the InhA:NADH binding reaction.

The derived amino acid sequence of the inhA gene predicted a segment whose sequence (GSSIVG) suggested that the protein would bind adenine nucleotides, i.e., a Rossman-fold. This possibility was tested by determining the binding of various adenine dinucleotides to the protein using microcalorimetry. Neither NADPH, NADP nor NAD exhibited significant binding to the inhA gene product, however, NADH exhibited tight and stoichiometric binding (see FIG. 2; $K_d$=2 $\mu$M).

This result suggested that the protein encoded by the inhA gene is an NADH-dependent reductase, and acts on compounds involved in fatty acid biosynthesis and elongation. A wide variety of unsaturated fatty acids were tested as substrates, as well as their coenzyme A derivatives. None were active as substrates for the protein in the presence of NADH, as measured spectrophotometrically at 340 nm. Acyl carrier protein (ACP) derivatives of various unsaturated fatty acids were prepared using commercially available preparations of E. coli ACP and acyl-ACP synthetase. The extent of coupling was assessed by determining the residual thiol content using Ellman's reagent (DTNB). Activity was demonstrated when unpurified preparations of 2-transoctenoyl-ACP was tested as a substrate, suggesting that the inhA gene product is a fatty acid enoyl-ACP reductase.

Figure 3A:
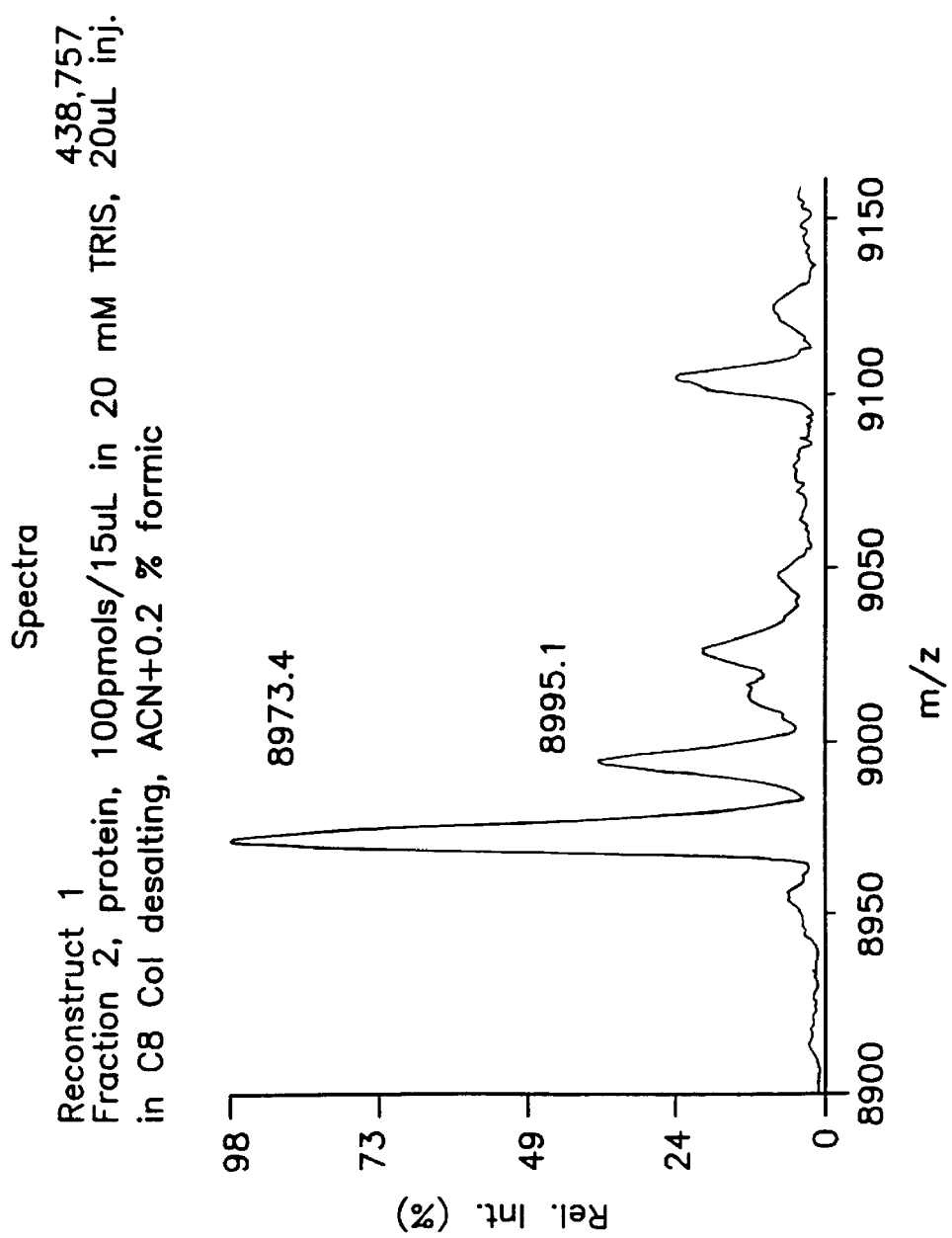
FIG. 3 represents electrospray-ionization mass spectrometric determination of a substrate, 2-transoctenoyl-ACP, and product, octanoyl-ACP, of the InhA-catalyzed reaction.
Figure 3B:
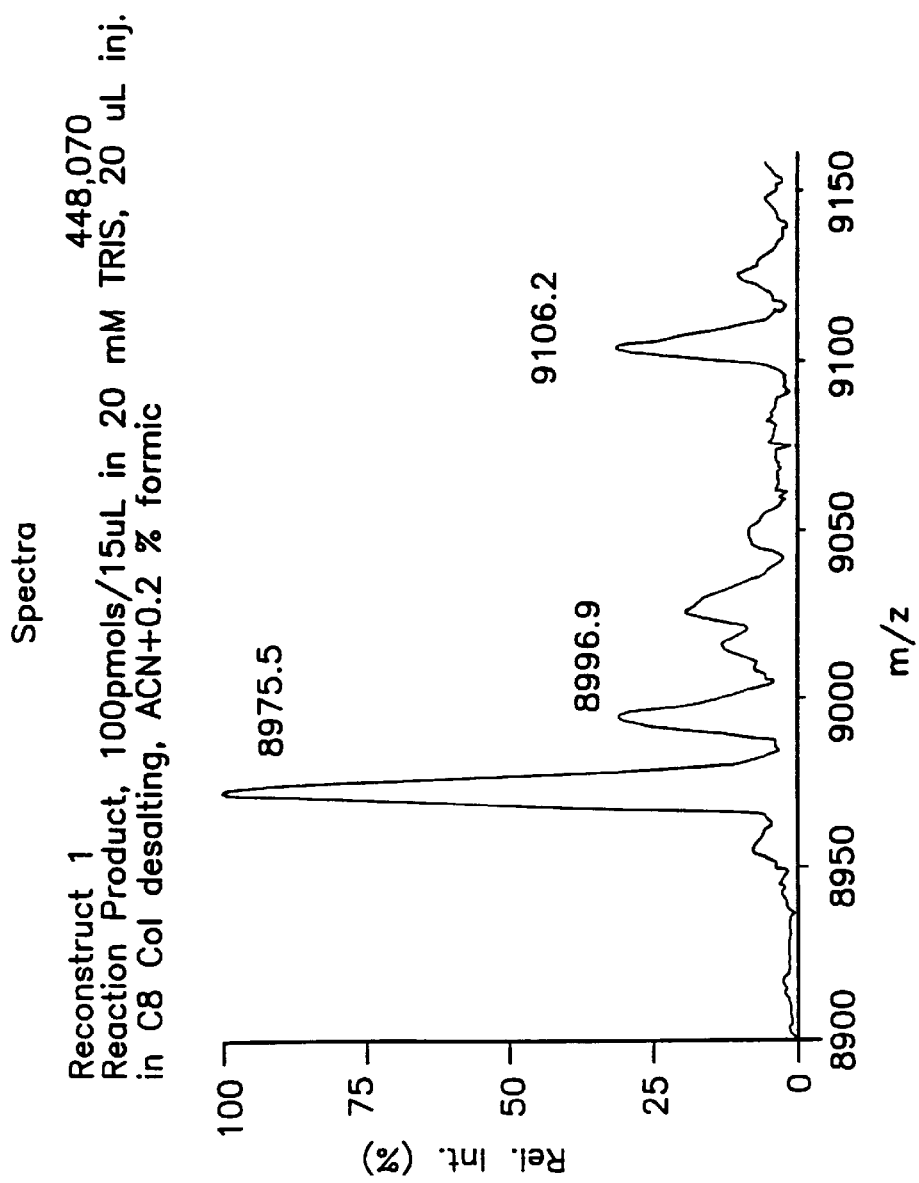

Purification of 2-transoctenoyl-ACP was performed on octyl-Sepharose. This material, and the precursor ACP, were analyzed by electrospray mass spectrometry. ACP exhibited a mass of 8,488 daltons, while the 2-transoctenoyl-ACP exhibited a mass of 8,973, as expected for the addition of the octenoate moiety to the covalently-bound pantothenate moiety of ACP (FIG. 3, panel A). The enzyme-catalyzed reduction of 2-transoctenoyl-ACP by NADH yields the saturated product, octanoyl-ACP, with a predicted molecular mass two mass units greater than 2-transoctenoyl-ACP. The mass spectrum showed that this prediction was borne out experimentally (see FIG. 3, panel B), with the des-methionyl, sodium salt, and full length ACP each being shifted by the predicted two mass units.

In order to demonstrate direct enzyme-catalyzed transfer of hydrogen, as a hydride ion, from NADH to 2-transoctenoyl-ACP, [4S-4-$^2$H] and [4R-4-$^2$H]NADH were prepared. No shift in the mass of the product octanoyl-ACP was observed with [4R-4-$^2$H]NADH as substrate, while an additional shift of one mass unit was observed using [4S-4-$^2$H]NADH as substrate for InhA due to the stereospecific transfer of the deuterium atom to the unsaturated enoyl-ACP substrate. Enoyl-CoA and enoyl-ACP reductases have previously been reported with both pro-R and pro-S stereospecificities.

The kinetic parameters for the inhA-catalyzed reduction of 2-transoctenoyl-ACP were determined spectrophotometrically by varying the concentration of either NADH, at a saturating concentration of 2-transoctenoyl-ACP, or by varying the concentration of 2-transoctenoyl-ACP, at a saturating concentration of NADH. Steady-state values of the $K_m$ for NADH and 2-transoctenoyl-ACP were determined to be 8 and 2 $\mu$M, respectively, and the maximum velocity was determined to be 1570 $\mu$M min$^{-1}$ mg$^{-1}$. These values may be compared to similar steady-state Michaelis constants for NADH and octenoyl-ACP for the Brassica enoyl-ACP reductase of 7.6 $\mu$M and <1 $\mu$M, respectively, and for the NADH-dependent enoyl-CoA reductase of M. smegmatis of 21 $\mu$M and 232 $\mu$M for NADH and octenoyl-CoA, respectively.

Figure 4:
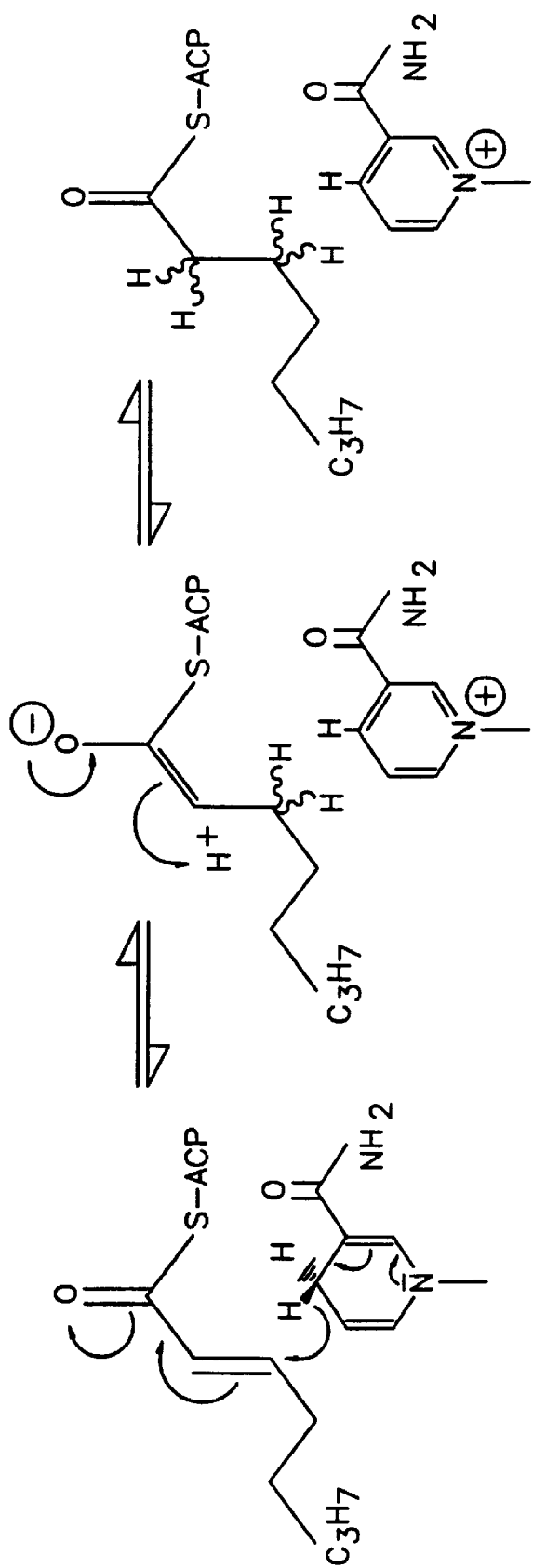
FIG. 4 represents the stereospecific NADH-dependent reduction of 2-transenoyl-ACPs by the direct transfer of the 4S hydrogen atom to the C3 position of the $\alpha$, $\beta$ unsaturated thioester catalyzed by InhA.

These data together suggest that the inhA gene product is an enzyme which catalyzes the stereospecific NADH-dependent reduction of 2-transenoyl-ACPs by the direct transfer of the 4S hydrogen atom to the C3 position of the alpha, beta unsaturated thioester (see FIG. 4). These results are in accord with previous stereochemical results obtained for pro- and eucaryotic enoyl-ACP and enoyl-CoA reductases. Strong evidence for the formation of an intermediate enolate anion has been shown by others. This intermediate collapses with the addition of a proton to the C2 position, which is acidic due to facile tautomerization occurring in thioesters. This chemistry also suggests a molecular mechanism for the interaction of isoniazid with the enzyme.

Isoniazid is known to be hydrolytically unstable in biological media, and the major metabolite of isoniazid is isonicotinic acid. Conjugation of this metabolite to ACP, catalyzed by an acyl-ACP synthetase, would form the isonicotinoyl-ACP. The planar pyridine ring could easily mimick the 2-transunsaturated fatty acyl moiety, and bind competitively to the inhA gene product, now identified as an enoyl-ACP reductase. Hence, one possible mechanism of INH action involves the sequential hydrolysis of the hydrazide to form the free acid, which is coupled to ACP by the mycobacterial ATP-dependent acyl-ACP synthetase, and inhibits the binding and reduction of enoyl-ACP's by the enoyl-ACP reductase encoded by the inhA gene. The mutation of Ser94 to an alanine residue may perturb the binding affinity of isonicotinoyl-ACP to the enzyme, thus decreasing the inhibition, and causing the resistance phenotype.

EXAMPLE 2

Figure 5:
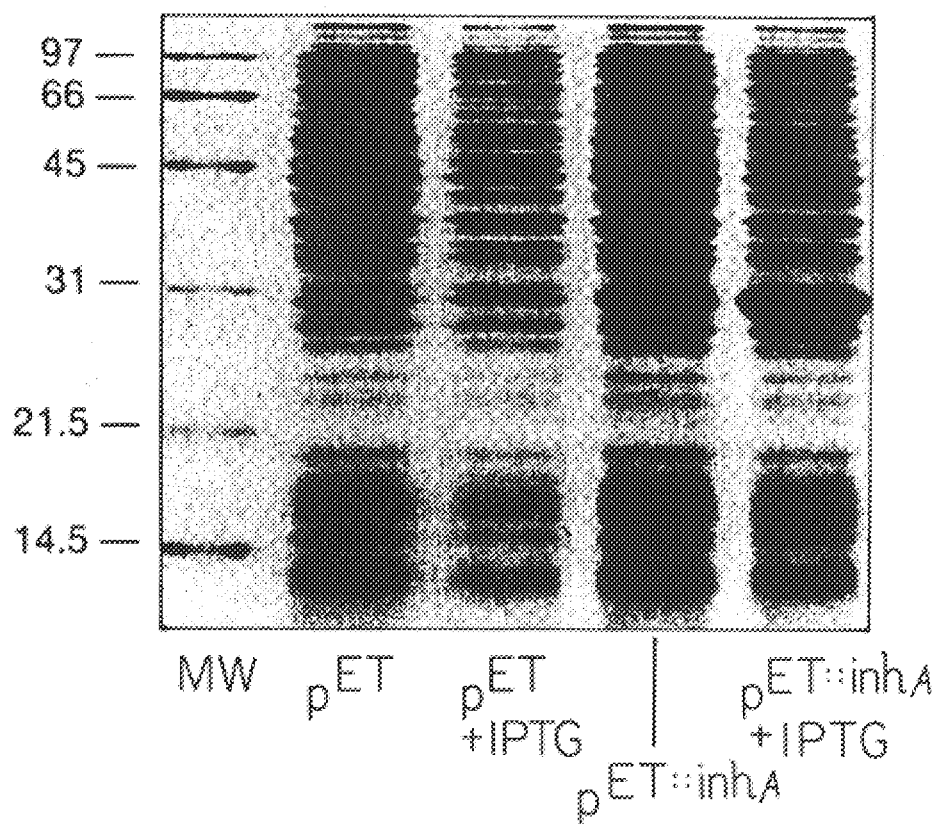
FIG. 5 represents the expression of the *M. tuberculosis* inhA gene in *E. coli;*

The M. tuberculosis inhA gene was fused to the ATG of the pET expression vector, pET-15b, by engineering a unique NcoI site into the inhA coding sequence. The resulting plasmid was transformed into a lambda lysogen containing the T7 polymerase fused to a lac-promoter which is inducible with IPTG. Upon induction, approximately 20% of the cell protein was a 32 kDa protein absent in uninduced cells (see FIG. 5). Cells containing the inhA gene inserted behind the T7 polymerase promoter were grown at 37° C. in rich media (2×YT, containing glycerol) to an optical density of 2–3. IPTG was added to a final concentration of 2 mM, and induction was continued for three hours. The cells were harvested, shell frozen and stored at −70° C. Cells were thawed in the presence of buffer containing a mixture of protease inhibitors, and disrupted by two passages through a French press. This material was centrifuged at 13,000 rpm to obtain a clear supernatant containing soluble InhA. The InhA enzyme was purified as described in Example 1.

Figure 6:
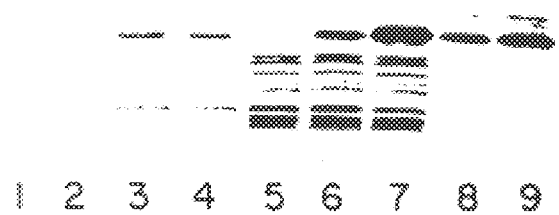
FIG. 6 represents a Western blot analysis using antibodies made with *E. coli*-produced InhA enzyme.

Polyclonal antibodies were prepared against the purified *M. tuberculosis* InhA protein in rabbits. A Western analysis was performed from lysates prepared from *M. smegmatis* cells and found to react with a 32 kDa protein found in *M. smegmatis* extracts and enriched in cell wall fractions used for the cell-free extract analysis. This confirmed that the purified recombinant InhA protein retains antigenic homologies with the native mycobacterial InhA protein (see FIG. 6).

EXAMPLE 3

It was determined that InhA specifically binds NADH. Analysis of the amino acid sequence of InhA revealed the presence of a NAD/NADH binding motif between residues 136–165. In order to test the ability of the protein to bind dinucleotide, purified recombinant InhA was subjected to a microcalorimetry based binding assay using a micocal omega II calorimeter (Micro-cal, Walthum Mass.). In this assay, a 100 $\mu$M solution of InhA was titrated with a variety of known dinucleotide co-factors (0.–100 $\mu$M final concentration). The experiments were performed at 37° C. in 50 mM Tris at pH 7.3. It was found that InhA binds two molecules of NADH per dimer of InhA. The binding constant was determined to be 2 $\mu$M. The enthalpy of binding was calculated to be −13.5 kcal/mol. These thermodynamic binding constants are consistent with previously determined kinetic constants for pyridine nucleotide-dependent enzymes. In contrast, NAD, NADP and NADPH failed to show appreciable binding affinity to InhA.

Because the inventors have determined that InhA enzyme mediates enoyl reductase activity, it is possible to develop methods of determining whether compounds are useful as bacteriocidal or herbicidal agents. If a compound is capable of inhibiting InhA-mediated enoyl reductase activity, then that compound will be an effective bacteriocide or herbicide. That compound can then be administered to treat bacterial infection or as a herbicide.

In order to determine whether a compound is useful as a bacteriocide or herbicide, InhA enzyme and a compound suspected of having bacteriocidal or herbicidal activity are combined. It is then determined whether the compound has inhibited InhA mediated enoyl reductase activity. If the compound has inhibited this activity, then the compound is useful as a bacteriocide or a herbicide. One means of determining whether a compound has inhibited InhA-mediated enoyl reductase activity is to determine whether the compound binds to InhA. If a compound binds to InhA, then that compound is useful as a bacteriocide or a herbicide as it inhibits InhA from mediating enoyl reductase activity in a bacteria or plant. The level of binding between a compound and InhA can be determined utilizing spectrophotometry, fluorescent labelling or radioactive labelling.

Another method of determining whether a compound is useful as a bacteriocide or a herbicide is combining InhA, NADH, enoyl S-ACP and a compound suspected of having bacteriocidal or herbicidal activity. Next, it is determined whether the compound had inhibited InhA-mediated enoyl reductase from occurring between the InhA, NADH, enoyl S-ACP. If such activity is inhibited, that compound is useful as a bacteriocidal agent or a herbicidal agent. It is possible to determine whether the compound inhibited InhA-mediated enoyl reductase activity by determining whether NAD is present, the presence of NAD indicating that enoyl reductase has occurred, and that the compound is not useful as a bacteriocide or a herbicide. Alternatively, it can be determined whether NADH is present. The presence of NADH indicating that enoyl reductase has not occurred, and that the compound is useful as a bacteriocide or a herbicide. The presence of either NAD or NADH can be detected utilizing a spectrophotometer.

Crystallization and determination of the crystalline space group, and preparation of heavy atom derivatives of the crystalline *M. tuberculosis* InhA protein were performed.

Example A

InhA Crystallization

Conditions for the crystallization of the recombinant *M. tuberculosis* InhA were discovered with Crystal Scan (Hampton research) and the hanging drop vapor diffusion method. Purified InhA was incubated with a 2-fold molar excess of NADH. Large crystals were obtained by adjusting the protein and precipitant concentrations in the hanging drop experiments, which were conducted at 24° C. Typically, 3 $\mu$l of a 20 mg/ml protein solution were mixed with 3 $\mu$l of precipitant solution containing 0.1M sodium citrate, 15–20% polyethylene glycol 4000, 7.5% isopropanol, pH 7.6. Plate-shaped crystals (dimensions 0.3 mm×0.5 mm×0.5 mm) were routinely produced in approximately 2 weeks, and they diffracted to better than 2.0 Å resolution.

Figure 7:
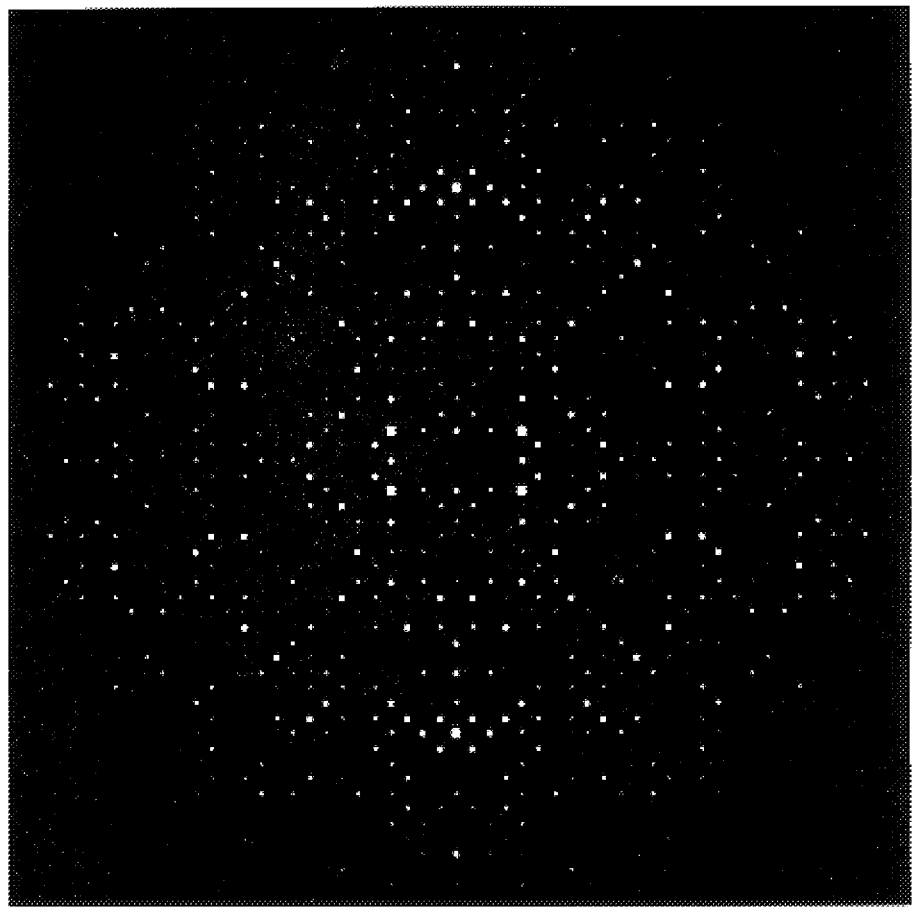
FIG. 7 represents an x-ray precession photograph of a C2 crystal of InhA.

A native diffraction data set was collected from a single crystal, 0.1 mm×0.4 mm×0.4 mm, so as to maximize the sampling of diffraction intensities in reciprocal space. A Siemens X1000 area detector system (Siemens, Madison, Wis.) was used to collect this data set, as well as all subsequent x-ray data. From the integrated and unreduced intensities, unit cell dimensions and space group symmetry were unambiguously deduced using XENGEN (Siemens) for data processing, PRECESS (courtesy of Dr. W. Furey, University of Pittsburgh) to view pseudo precession photographs and XPREP (Siemens) to verify the space group symmetry. The space group was determined to be C2. FIG. 7 represents an x-ray precession photograph of a C2 crystal of InhA. The C2 crystals have the following unit cell dimensions: a=101.1 Å, b=83.4 Å, c=192.9 Å, $\beta$=95°, and $\alpha$=$\gamma$=90°. Assuming the presence of 6 InhA monomers per symmetric unit, a $V_m$ of 2.12 was calculated, which is consistent with a solvent content of about 43%, a value typical for proteins of this molecular weight. The results of data collection and reduction are summarized in Table 1.

TABLE 1

Data collection for InhA

| DATA | NATIVE 1 | NATIVE 2 | PCMBS | NATIVE 3 | PCMPS | $C_4H_6HgO_4$ | $C_4H_6PbO_4$ |
|---|---|---|---|---|---|---|---|
| Space Group | C2 | $P2_1$ | $P2_1$ | $P6_222$ | $P6_222$ | $P6_222$ | $P6_222$ |
| Unit Cell dimensions (Å) | a = 101.3 | a = 69.4 | a = 69.2 | a = 100.1 | a = 99.7 | a = 100.3 | a = 100 |
|  | b = 83.5 | b = 115.9 | b = 115.2 | b = 100.1 | b = 99.7 | b = 100.3 | b = 100 |
|  | c = 193.3 | c = 65.5 | c = 65.6 | c = 140.1 | c = 140.3 | c = 140.1 | c = 140.1 |
|  | α = 90.0° | α = 90.0° | α = 90.0° | α = 90.0° | α = 90.0° | α = 90.0° | α = 90.0° |
|  | β = 96.1° | β = 97.1° | β = 97.9° | β = 90.0° | β = 90.0° | β = 90.0° | β = 90.0° |
|  | γ = 90.0° | γ = 90.0° | γ = 90.0° | γ = 120.0° | γ = 120.0° | γ = 120.0° | γ = 120.0° |
| $R_{symm}$(%) | 8.6 | 4.9 | 11.2 | 9.6 | 13.9 | 14.3 | 13.6 |
| I/σI | 8.4 | 12.7 | 5.6 | 6.9 | 4.3 | 3.7 | 4.3 |
| Unique reflections | 20607 | 27548 | 25431 | 23880 | 26375 | 26261 | 26415 |
| $R_{merge}$(%) |  |  | 13 |  | 10.7 | 10.6 | 9.5 |
| Resolution (Å) | 20–2.61 | 20–2.49 | 20–2.25 | 20–2.1 | 20–2.52 | 20–2.53 | 20–2.52 |

EXAMPLE B

InhA Crystallization

Figure 8:
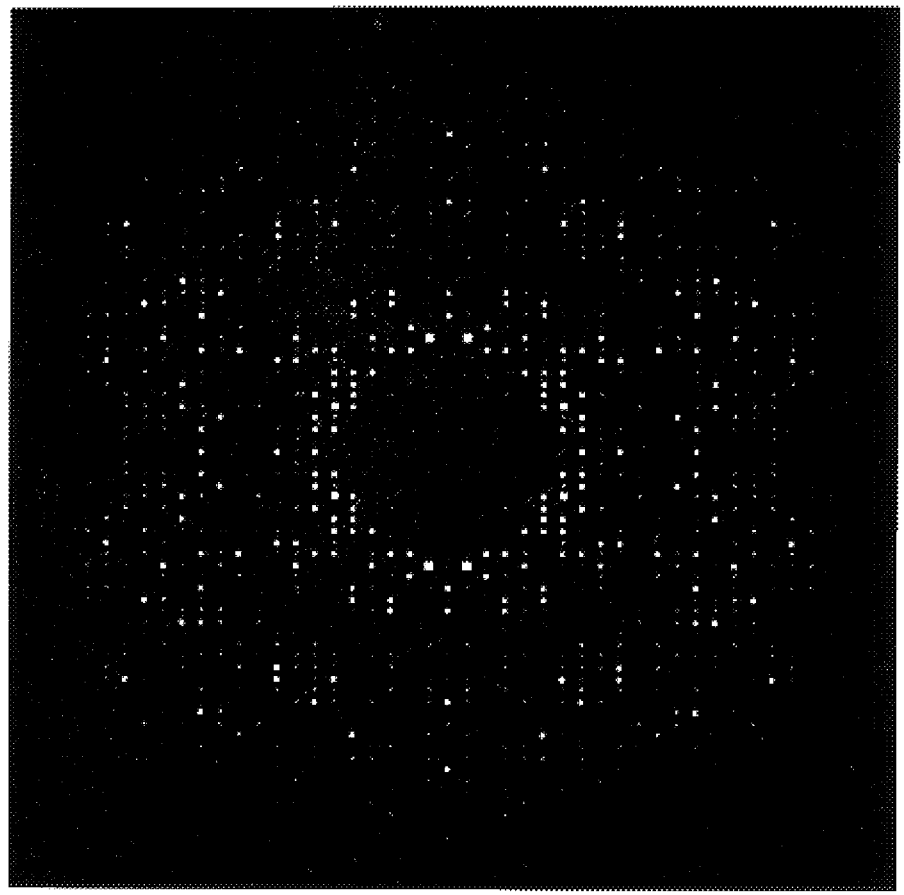
FIG. 8 represents and x-ray precession photograph of a P2$_1$ crystal of InhA.
Figure 9A:
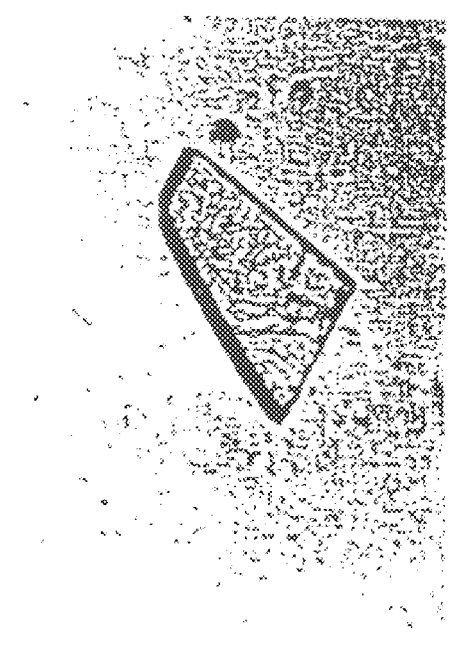
FIG. 9 represents the monoclinic crystal of InhA protein crystallized in space group C2 (left panel) and the monoclinic crystal of InhA protein crystallized in space group P2$_1$ (right panel)
Figure 9B:
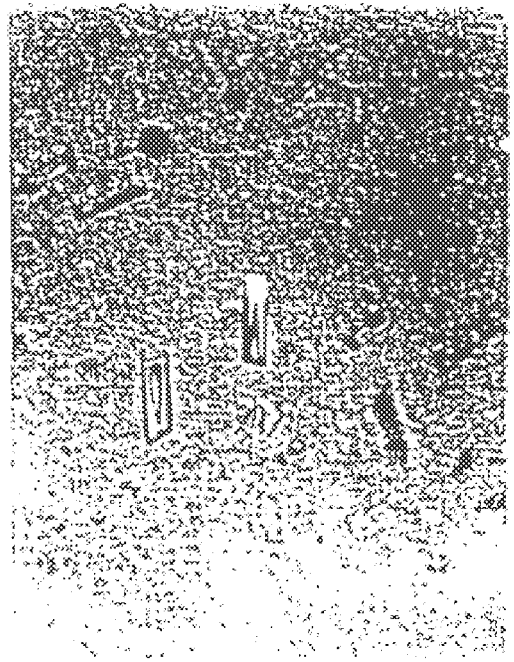

Crystals with a different morphology appeared in hanging drop experiments under similar conditions with the exception that they did not contain isopropanol. These crystals were parallelepiped in shape, and obtained a maximum size of about 0.3 mm×0.3 mm×0.6 mm. Oscillation images of these crystals suggested that they had different unit cell parameters than the C2 space group crystals described in Example A. A highly redundant data set collected on these crystals was used to calculate the unit cell dimensions and space group symmetry. FIG. 8 represents an x-ray precession photograph of a $P2_1$ crystal of InhA. The unit cell dimensions were determined to be a=69 Å, b=116 Å, c=65 Å, β=97.8°, and α=γ=90°. Systematically absent reflections with the Miller indices OKO=odd indicated that the space group is $P2_1$. These crystals also diffract to better than 2.0 Å resolution and contain four InhA monomers per asymmetric unit (see FIG. 9).

Both native data sets of the two crystalline Inh:NADH complexes proved to be of sufficient quality and completeness to be used in further structural analyses. Since this set of crystals had a more manageable unit cell than those described above, one with a shorter maximum unit cell dimension length and fewer molecules in the asymmetric unit, a heavy atom derivative search with this crystal form was performed. The statistics which describe the native and heavy atom diffraction data are found in Table 1.

In order to determine the three dimensional structure of InhA, isomorphous replacement can be utilized. Isomorphous replacement remains the method of choice for solving an unknown protein structure when no homologous protein structure is available. In this method, heavy atom derivatives of the native crystals are prepared by either soaking crystals of the native protein with solutions of heavy atom salts or by pre-reacting protein with heavy atoms prior to crystallization. The contribution of the heavy atom to the diffraction intensity of the crystal is used to produce the phase angle of the native diffracted x-rays. This information is required in order to determine the electron density of the crystal's unit cell. For InhA, 2 heavy atom soaked crystals have been prepared. The first was a 1 mM phenyl chloromercury benzene sulphonate (PCMBS) soaked crystal. The data collected from this crystal indicated that it serves as a good heavy atom derivative; the R-factor between the native and PCMBS crystal was 13%, based on intensity. Four heavy atom sites in the PCMBS soaked crystal (possibly one site per monomer) have been determined and confirmed using a difference Patterson map and self-difference Fourier maps, phased by pairs of the four heavy atom sites.

Although density modification methods (e.g., solvent levelling and molecular averaging) have been used with single heavy stom derivative (SIR) information to produce interpretable electron density maps, it is desirable to have at least two heavy atom derivatives. This is due to a phase angle ambiguity which arises from SIR data alone, commonly referred to as the "phase problem".

EXAMPLE C

InhA Crystallization

The hanging drop method was utilized to obtain inhA crystals. In this procedure, 3 μl of protein solution (with a 2:1 NADH:protein molar ratio) were mixed with 3 μl of the precipitant solution on a silanized coverslip, which was subsequently inverted and sealed above 700 μl of the precipitant solution. The precipitant solution consisted of methyl pentane diol (MPD) at concentrations ranging from 6 to 12% (v/v), with the best results being obtained at 10%. Sodium citrate at a concentration of 0.1 to 0.2M may be used for this purpose, while a sodium HEPES solution is also employed at a concentration of 0.1M. In addition, sodium citrate may be replaced by sodium acetate for this purpose. The preferred pH for crystal growth is in the range of 6 to 8.5, and is optimal at 7.2. InhA was provided in the form of aqueous solution (in 10 mM sodium HEPES, pH 7.2) at a concentration of up to 13 mg/ml, with best results being obtained at 10 mg/ml.

Figure 10:
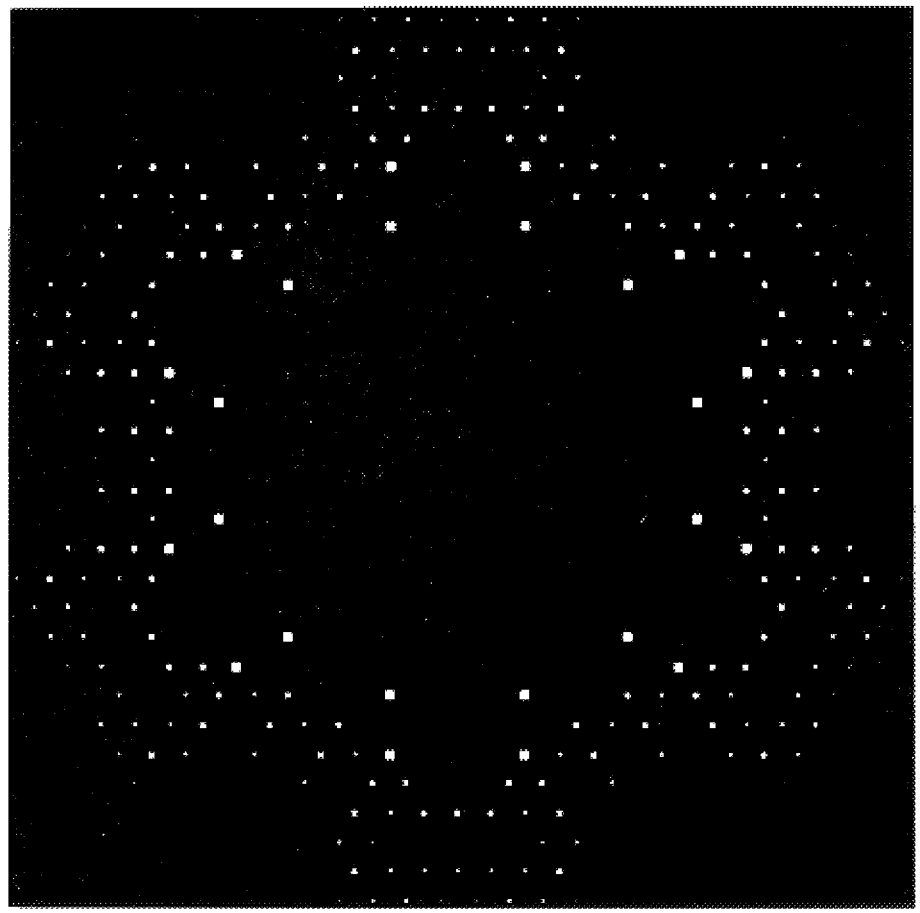
FIG. 10 represents an x-ray precession photograph of a P6$_2$22 crystal of InhA.

InhA crystals appeared overnight, and continued growth for up to 2 weeks to dimensions of 0.5×0.5×0.2 mm. For x-ray diffraction experiments the crystals were transferred from the hanging drop to a 1.0 mm capillary, whose ends were filled with precipitant solution and sealed with wax, and mounted onto the x-ray diffractometer. FIG. 10 is an x-ray precession photograph of an InhA crystal.

The inhA crystals appeared in the form of hexagonal structures, with the space group $P6_222$. Unit cell constants are: a=b=100.14 Å, c=140.4 Å, α=β=90° and γ=120°. These crystals can readily be grown to approximately 0.5 mm in size in two dimensions, and 0.2 mm in thickness. The InhA crystals of this invention are suitable for x-ray diffraction studies, and therefore can be used to determine the three dimensional structure of InhA enzyme.

Three heavy derivatives (p-(chloromercury)-phenyl sulfonate, PCMPS; mercury acetate; and lead acetate) of the P6$_2$22 crystals of InhA were used to determine the three dimensional structure of InhA. The lead derivative was collected after a native crystal, originally produced in the presence of a 2:1 NADH:protein ratio, was soaked overnight in 1 mM C$_4$H$_6$O$_4$Pb in 0.1M Na acetate, 0.1M Na HEPES, 10% MPD (methyl pentane diol), pH 6.5. The mercury derivative was collected after a native crystal grown in the same fashion was soaked overnight in 1 mM C$_4$H$_6$O$_4$Hg in 0.1 Na citrate, 0.1M Na HEPES, 10% MPD, pH 7.2. The PCMPS derivative was obtained by mixing the protein (10 mg/mL in 10 mM HEPES, pH 7.2) with a 6-fold molar excess of PCMPS overnight at 19° C. and then crystallization the complex under the same conditions that gave native crystals. A heavy atom derivative of InhA with PCMPS could also be obtained by utilizing the same procedure as in the lead acetate experiment, but with lower metal occupancy. Crystals of the InhA-PCMPS were hexagonal with the native form and could then be used in the MIR procedures.

Figure 11:
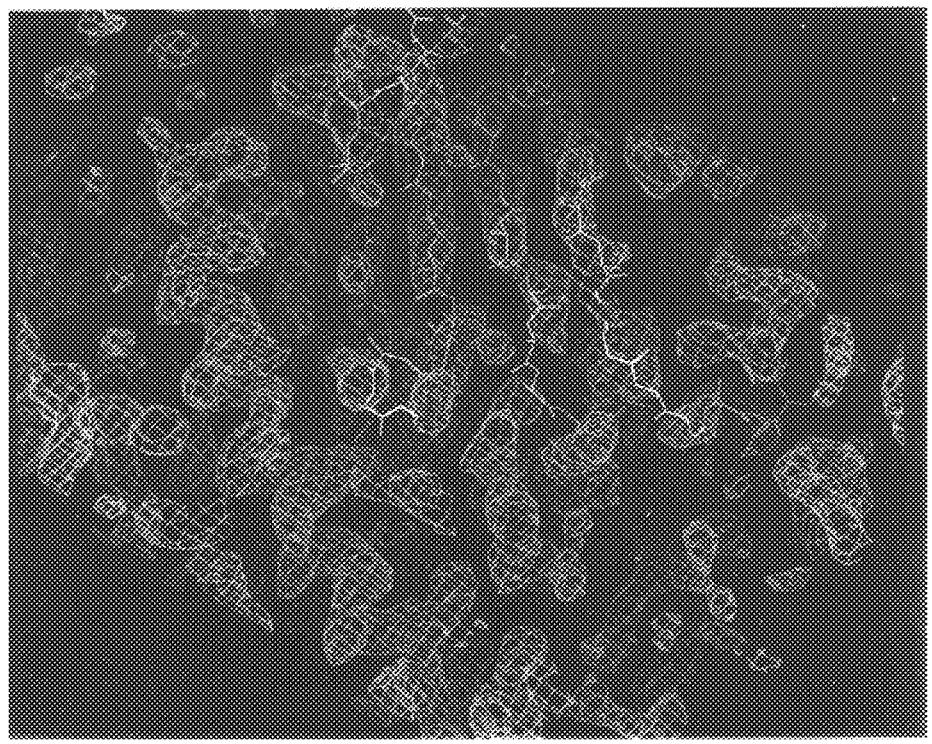
FIG. 11 represents a portion of the electron density map of the P6$_2$22 crystals of InhA calculated using heavy atom derivatives prepared in accordance with the invention.

Heavy atom binding positions were found using Patterson maps. The heavy atom binding positions (as calculated from difference Patterson maps) were refined by an iterative series of phase refinement, using the package PHASES (W. Furey, VA Medical School and University of Pittsburgh, Pa.), running on a Silicon Graphics Iris computer. Solvent flattening (Wang, 1985) procedures, as implemented in PHASES, were used to further improved the MIR phases. From the resulting electron density map (up t 2.8 A), a partial model of InhA was built. FIG. 11 represents a portion of the electron density map of a P6$_2$22 crystal of InhA calculated using heavy atom derivatives.

Once the three dimensional structure of InhA enzyme is obtained, compounds which inhibit its biochemical activity can be produced. Once such compounds are put into contact with InhA, InhA cannot produce mycolic acids, which are essential for cell survival. Hence, this will result in death of mycobacterial cells and plant cells. Compounds which inhibit the biochemical activity of InhA enzyme are administered to treat mycobacterial infection, including infection caused by *M. tuberculosis*. In addition, such compounds can be used as herbicides. Such compounds could be administered orally, enterally, intraperitoneally, subcutaneously, intravenously or by other modes known to those skilled in the art to treat bacterial infection, or can be administered by spraying as herbicides.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for determining whether a compound is useful as a bacteriocide or a herbicide comprising (i) combining InhA enzyme and a compound suspected of having bacteriocidal or herbicidal activity, wherein said compound is present in an amount effective to inhibit InhA-mediated enoyl reductase activity, and (ii) determining whether said compound inhibits InhA-mediated enoyl reductase activity by measuring the level of binding causing inhibition of InhA-mediated enoyl reductase activity which indicates the utility of said compound as a bacteriocide or a herbicide.

2. The method of claim 1 wherein InhA-mediated enoyl reductase activity inhibition is determined by microcalorimetrically measuring the level of binding between said compound and InhA enzyme.

3. The method of claim 1 wherein InhA-mediated enoyl reductase activity inhibition is determined by measuring the level of binding between said compound and InhA by a method selected from the group consisting of spectrophotometry, fluorescent labelling and radioactive labelling.

4. A method for determining whether a compound is useful as a bacteriocide or a herbicide comprising (i) combining InhA, NADH, enoyl S-ACP and a compound suspected of having bacteriocidal or herbicidal activity, wherein said compound is present in an amount effective to inhibit binding of an InhA-NADH complex to enoyl S-ACP, and (ii) determining whether said compound inhibits binding of the InhA-NADH complex to enoyl S-ACP, whereby inhibition of binding of the InhA-NADH complex to enoyl S-ACP indicates that said compound is useful as a bacteriocide or a herbicide.

5. The method of claim 4 wherein the inhibition of binding of the InhA-NADH complex to enoyl S-ACP is determined by measuring NAD produced whereby the production of NAD indicates that binding of the InhA-NADH complex to enoyl S-ACP has not been inhibited.

6. The method of claim 5 wherein the presence of NAD is determined utilizing a spectrophotometer.

7. The method of claim 4 wherein the inhibition of binding of the InhA-NADH complex to enoyl S-ACP is determined by measuring NADH present whereby the presence of NADH indicates that binding of the InhA-NADH complex to enoyl S-ACP has been inhibited.

8. The method of claim 7 wherein the presence of NADH is determined utilizing a spectrophotometer.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 3120
        ( B ) TYPE: nucleic acid
        ( C ) STRANDEDNESS: single
        ( D ) TOPOLOGY: both ( i i ) MOLECULE TYPE: DNA
        ( A ) DESCRIPTION:

( i i i ) HYPOTHETICAL: No ( i v ) ANTI-SENSE:

( v ) FRAGMENT TYPE:

( v i ) ORIGINAL SOURCE: inhA operon
        ( A ) ORGANISM: M tuberculosis
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE: M tuberculosis ( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:

( C ) IDENTIFICATION METHOD:
( D ) OTHER INFORMATION:

( x ) PUBLICATION INFORMATION: None
    ( A ) AUTHORS:
    ( B ) TITLE:
    ( C ) JOURNAL:
    ( D ) VOLUME:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO: 1:

```
AGCGCGACAT  ACCTGCTGCG  CAATTCGTAG  GGCGTCAATA  CACCCGCAGC  CAGGGCCTCG    60
CTGCCCAGAA  AGGGATCCGT  CATGGTCGAA  GTGTGCTGAG  TCACACCGAC  AAACGTCACG   120
AGCGTAACCC  CAGTGCGAAA  GTTCCGCCG   GAAATCGCAG  CCACGTTACG  CTCGTGGACG   180
TACCGATTTC  GGCCCGGCCG  CGGCGAGACG  ATAGGTTGTC  GGGGTGACTG  CCACAGCCAC   240
TGAAGGGGCC  AAACCCCCAT  TCGTATCCCG  TTCAGTCCTG  GTTACCGGAG  GAAACCGGGG   300
GATCGGGCTG  GCGATCGCAC  AGCGGCTGGC  TGCCGACGGC  CACAAGGTGG  CCGTCACCCA   360
CCGTGGATCC  GGAGCGCCAA  AGGGGCTGTT  TGGCGTCGAA  TGTGACGTCA  CCGACAGCGA   420
CGCCGTCGAT  CGCGCCTTCA  CGGCGGTAGA  AGAGCACCAG  GGTCCGGTCG  AGGTGCTGGT   480
GTCCAACGCC  GGCCTATCCG  CGGACGCATT  CCTCATGCGG  ATGACCGAGG  AAAAGTTCGA   540
GAAGGTCATC  AACGCCAACC  TCACCGGGGC  GTTCCGGGTG  GCTCAACGGG  CATCGCGCAG   600
CATGCAGCGC  AACAAATTCG  GTCGAATGAT  ATTCATAGGT  TCGGTCTCCG  GCAGCTGGGG   660
CATCGGCAAC  CAGGCCAACT  ACGCAGCCTC  CAAGGCCGGA  GTGATTGGCA  TGGCCCGCTC   720
GATCGCCCGC  GAGCTGTCGA  AGGCAAACGT  GACCGCGAAT  GTGGTGGCCC  CGGGCTACAT   780
CGACACCGAT  ATGACCCGCG  CGCTGGATGA  GCGGATTCAG  CAGGGGGCGC  TGCAATTTAT   840
CCCAGCGAAG  CGGGTCGGCA  CCCCCGCCGA  GGTCGCCGGG  GTGGTCAGCT  TCCTGGCTTC   900
CGAGGATGCG  AGCTATATCT  CCGGTGCGGT  CATCCCGGTC  GACGGCGGCA  TGGGTATGGG   960
CCACTGACAC  AACACAAGGA  CGCACATGAC  AGGACTGCTG  GACGGCAAAC  GGATTCTGGT  1020
TAGCGGAATC  ATCACCGACT  CGTCGATCGC  GTTTCACATC  GCACGGGTAG  CCCAGGAGCA  1080
GGGCGCCCAG  CTGGTGCTCA  CCGGGTTCGA  CCGGCTGCGG  CTGATTCAGC  GCATCACCGA  1140
CCGGCTGCCG  GCAAAGGCCC  CGCTGCTCGA  ACTCGACGTG  CAAAACGAGG  AGCACCTGGC  1200
CAGCTTGGCC  GGCCGGGTGA  CCGAGGCGAT  CGGGGCGGGC  AACAAGCTCG  ACGGGGTGGT  1260
GCATTCGATT  GGGTTCATGC  CGCAGACCGG  GATGGGCATC  AACCCGTTCT  TCGACGCGCC  1320
CTACGCGGAT  GTGTCCAAGG  GCATCCACAT  CTCGGCGTAT  TCGTATGCTT  CGATGGCCAA  1380
GGCGCTGCTG  CCGATCATGA  ACCCCGGAGG  TTCCATCGTC  GGCATGGACT  CGACCCGAG   1440
CCGGGCGATG  CCGGCCTACA  ACTGGATGAC  GGTCGCCAAG  AGCGCGTTGG  AGTCGGTCAA  1500
CAGGTTCGTG  GCGCGCGAGG  CCGGCAAGTA  CGGTGTGCGT  TCGAATCTCG  TTGGCGCAGG  1560
CCCTATCCGG  ACGCTGGCGA  TGAGTGCGAT  CGTCGGCGGT  GCGCTCGGCG  AAGAGGCCGG  1620
CGCCCAGATC  CAGCTGCTCG  AGGAGGGCTG  GGATCAGCGC  GCTCCGATCG  GCTGGAACAT  1680
GAAGGATGCG  ACGCCGGTCG  CCAAGACGGT  GTGCGCGCTG  CTGTCTGACT  GGCTGCCGGC  1740
GACCACGGGT  GACATCATCT  ACGCCGACGG  CGGCGCGCAC  ACCCAATTGC  TCTAGAACGC  1800
ATGCAATTTG  ATGCCGTCCT  GCTGCTGTCG  TTCGGCGGAC  CGGAAGGGCC  CGAGCAGGTG  1860
CGCCCGTTCC  TGGAGAACGT  TACCCGGGGC  CGCGGTGTGC  CTGCCGAACG  GTTGGACGCG  1920
```

-continued

| | | | | | | |
|---|---|---|---|---|---|---|
| GTGGCCGAGC | ACTACCTGCA | TTTCGGTGGG | GTATCACCGA | TCAATGGCAT | TAATCGCACA | 1980 |
| CTGATCGCGG | AGCTGGAGGC | GCAGCAAGAA | CTGCCGGTGT | ACTTCGGTAA | CCGCAACTGG | 2040 |
| GAGCCGTATG | TAGAAGATGC | CGTTACGGCC | ATGCGCGACA | ACGGTGTCCG | GCGTGCAGCG | 2100 |
| GTCTTTGCGA | CATCTGCGTG | GAGCGGTTAC | TCGAGCTGCA | CACAGTACGT | GGAGGACATC | 2160 |
| GCGCGGCCCC | CCGCGCGGCC | GGGCGCGACG | CGCCTGAACT | GGTAAAACTG | CGGCCCTACT | 2220 |
| TCGACCATCC | GCTGTTCGTC | GAGATGTTCG | CCGACGCCAT | CACCGCGGCC | GCCGCAACCG | 2280 |
| TGCGCGGTGA | TGCCCGGCTG | GTGTTCACCG | CGCATTCGAT | CCCGACGGCC | GCCGACCACC | 2340 |
| GCTGTGGCCC | CAACCTCTAC | AGCCGCCAAG | TCGCCTACGC | CACAAGGCTG | GTCGCGGCCG | 2400 |
| CTGCCGGATA | CTGCGACTTT | GACCTGGCCT | GGCAGTCGAG | ATCGGGCCCG | CCGCAGGTGC | 2460 |
| CCTGGCTGGA | GCCAGACGTT | ACCGACCAGC | TCACCGGTCT | GGCTGGGGCC | GGCATCAACG | 2520 |
| CGGTGATCGT | GTGTCCCATT | GGATTCGTCG | CCGACCATAT | CGAGGTGGTG | TGGGATCTCG | 2580 |
| ACCACGAGTT | GCGATTACAA | GCCGAGGCAG | CGGGCATCGC | GTACGCCCGG | GCCAGCACCC | 2640 |
| CCAATGCCGA | CCCGCGGTTC | GCTCGACTAG | CCAGAGGTTT | GATCGACGAA | CTCCGTTACG | 2700 |
| GCCGTATACC | TGCGCGGGTG | AGTGGCCCCG | ATCCGGTGCC | GGGCTGTCTG | TCCAGCATCA | 2760 |
| ACGGCCAGCC | ATGCCGTCCG | CCGCACTGCG | TGGCTAGCGT | CAGTCCGGCC | AGGCCGAGTG | 2820 |
| CAGGATCGCC | GTGACCGCGG | ACATCCGGGC | CGAGCGCACC | ACGGCGGTCA | ACGGTCTCAA | 2880 |
| CGCATCGGTG | GCACGCTGAG | CGTCCGACAA | CGACTGCGTT | CCGATCGGCA | ATCGACTCAG | 2940 |
| CCCGGCACTG | ACCGCGATGA | TCGCATCGAC | GTGCGCGGCA | TTCTCGAGCA | CCCGCAATGC | 3000 |
| GCGCGATGGC | GCGTGGTCGG | GAACCCGGTG | TTGCCGTGAC | GATTCGAGCA | ACTGCTCGAC | 3060 |
| GAGGCCACGG | GGCTTGGCGA | CGTCGCTAGA | TCCCAGTCCG | ATGGTGCTCA | AGGCTTCGGC | 3120 |